United States Patent [19]

Karjalainen et al.

[11] Patent Number: 4,910,214

[45] Date of Patent: Mar. 20, 1990

[54] OPTICAL ISOMER OF AN IMIDAZOLE DERIVATIVE MEDETOMIDINE AS AN ALPHA-2-RECEPTOR AGONIST

[75] Inventors: Arto J. Karjalainen, Oulu; Raimo E. Virtanen, Rusko; Eino J. Savolainen, Oulu, all of Finland

[73] Assignee: Farmos Yhtyma Oy, Turku, Finland

[21] Appl. No.: 219,637

[22] Filed: Jul. 15, 1988

[30] Foreign Application Priority Data

Jul. 16, 1987 [GB] United Kingdom ............... 8716803

[51] Int. Cl.$^4$ .................... A61K 31/415; C07D 233/58
[52] U.S. Cl. .................................... 514/396; 548/335
[58] Field of Search ......................... 548/335; 514/396

[56] References Cited

U.S. PATENT DOCUMENTS 4,544,664 10/1985 Karjalainen et al. ............... 514/400

FOREIGN PATENT DOCUMENTS 0024829 3/1981 European Pat. Off. .
0058047 8/1982 European Pat. Off. .
0072615 2/1983 European Pat. Off. .
02114528 3/1987 European Pat. Off. .

OTHER PUBLICATIONS

*Chemical Abstracts*, 105: 183977c (1986) [JPN. Kokai 61, 134, 314, Farmos, 6/21/86].

Noller, C., *Chemistry of Carbon Compounds*, 2nd Ed., W. B. Saunders, Philadelphia, 1957, pp. 341–344.

*Primary Examiner*—Richard A. Schwartz
*Attorney, Agent, or Firm*—Armstrong, Nikaido, Marmelstein, Kubovcik & Murray

[57] ABSTRACT

The separated d and l enantiomers of medetomidine and their salts are selective and potent $\alpha_2$-receptor agonists.

4 Claims, No Drawings

OPTICAL ISOMER OF AN IMIDAZOLE DERIVATIVE MEDETOMIDINE AS AN ALPHA-2-RECEPTOR AGONIST

This invention relates to optical isomers of imidazole derivatives and to their preparation.

Medetomidine which has the formula:

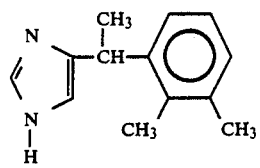

is known as a selective and potent $\alpha_2$-receptor agonist. It has been described, e.g. in European Patent Publication No. 72615, as an antihypertensive agent and in the European Patent Publication No. 187471 as a veterinary sedative-analgesic agent.

The present invention provides, as new compounds, the optically active d- and l-enantiomers of medetomidine, and their non-toxic pharmaceutically acceptable acid addition salts. These compounds may be represented by the formulae:

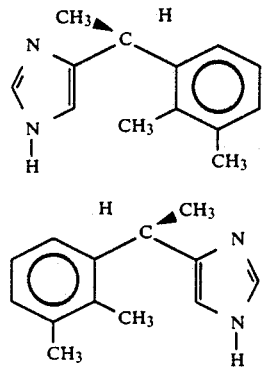

According to a feature of the invention, racemic medetomidine is separated into the enantiomers II and III by conversion of the racemate into a mixture of diastereoisomers and separating the latter by fractional crystallization. Since medetomidine is a base, it may be converted into a diastereoisomer salt mixture by reaction with an optically active acid such as (+)-tartaric acid. Other useful optically active acids are, e.g., (−)-malic acid, (−)-mandelic acid and (+)-camphor-10-sulfonic acid. (+)-Tartaric acid is especially useful for the resolution. The separation of the diastereisomers is performed by repeated crystallizing from an alcohol such as methanol or ethanol or a mixture of them.

Once the diastereoisomers have been separated the acid addition salts can be converted back to the free bases by making their aqueous solutions alkaline with sodium hydroxide and by extracting the liberated base in an appropriate organic solvent such as methylene chloride.

The d- and l-enantiomers of medetomidine react with organic and inorganic acids to form the corresponding acid addition salts, which have the same therapeutic activities as the bases. They can thus form many pharmaceutically usable acid addition salts, as, for instance, chlorides, bromides, sulfates, nitrates, phosphates, sulfonates, formates, tartrates, maleates, citrates, benzoates, salicylates, ascorbates and the like.

The d- and l-enantiomers of medetomidine are selective and potent $\alpha_2$-receptor agonists.

Adrenergic receptors are physiologically important binding sites which are specific to noradrenaline and adrenaline and located on the surface of the cell membrane. The adrenoceptors of the sympathetic nervous system have been classified into two different subtypes, alpha-($\alpha$) and beta-($\beta$) receptors, which can be further divided into two subgroups, viz $\alpha_1$ and $\alpha_2$ and $\beta_1$ and $\beta_2$. Of these receptor types, $\beta_1$, $\beta_2$ and $\alpha_1$ are mainly located post-synaptically on the surface of, e.g., smooth muscle and thus mediate, e.g., smooth muscle contraction or relaxation; whereas $\alpha_2$ receptors are mainly located presynaptically on the terminals of noradrenergic nerves. If $\alpha_2$-receptors are stimulated by noradrenaline under physiological conditions noradrenaline release is blocked, i.e. there is a negative feed-back phenomenon. This negative feed-back phenomenon may also be induced by certain synthetic $\alpha_2$-agonists like medetomidine and some of its near derivatives.

In animal experiments, the d- and l- enantiomers of the present invention and especially the d-enantiomer, have proved to possess highly enhanced $\alpha_2$-selectivity and potency compared to the racemic mixture (i.e. medetomidine). The d-enantiomer can be expected to be of value, e.g., as a sedative-analgesic, anxiolytic or antihypertensive agent. Furthermore, it can be used as a pharmacological tool in the study of the physiology and pharmacology of $\alpha_2$-adrenoceptors.

The pharmacological activity of the compounds of the invention was determined as follows:

1. ALPHA-2 AGONISM IN VITRO $\alpha_2$-agonism was determined by means of isolated, electrically stimulated mouse was deferens preparation (Marshall et al., Br. J. Pharmac. 62, 147–151, 1978). In this model, an $\alpha_2$-agonist is able to block electrically induced muscular contractions by activating the presynaptic $\alpha_2$-adrenoceptors and thus diminishing the secretion on the motor transmitter. Known $\alpha_2$-agonists like detomidine, medetomidine and clonidine were used as reference substances. Results are shown in Table 1, where the $\alpha_2$-agonist effect is presented as the $pD_2$-value (negative logarith of the molar concentration of the compound producing 50 percent of maximal inhibition.)

TABLE 1

| Compound | $\alpha_2$-agonism in vitro (mouse vas deferens). $pD_2$ |
|---|---|
| d-enantiomer | 9.3 |
| l-enantiomer | 6.0 (partial agonist) |
| medetomidine | 9.0 |
| detomidine | 8.5 |
| clonidine | 8.5 |

These results show that the $\alpha_2$-agonist activity of medetomidine is limited to the d-enantiomer. The d-enantiomer shows an enhanced $\alpha_2$-agonist activity compared to the outer agents studied.

2. $\alpha_2/\alpha_1$-SELECTIVITY IN VITRO

The selectivity of the d-enantiomer as an $\alpha_2$-agonist was studied in receptor binding experiments using rat brain membranes. The ability of the d-isomer and the reference compounds to compete with $^3$H-clonidine (for $\alpha_2$-receptors) and $^3$H-prazosin (for $\alpha_1$-receptors) was studied essentially as described by Virtanen and Nyman in Eur. J. Pharmac. 108, 163–9, 1985. Results of the test are presented in Table 2, where the ability of the studied agents to compete with $^3$H-clonidine and $^3$H-prazosin binding is expressed as the IC$_{50}$-value (molar concentration of the competing ligand needed to displace 50 percent of the radioactive ligand).

TABLE 2

| Compound | $^3$H-clonidine displacement IC$_{50}$, nM | $^3$H-prazosin displacement IC$_{50}$, nM | $\alpha_2/\alpha_1$-selectivity |
| --- | --- | --- | --- |
| d-enantiomer | 1.2 | 55019 | 45849 |
| l-enantiomer | 46 | 189975 | 4129 |
| medetomidine | 3.3 | 16700 | 5060 |
| detomidine | 3.7 | 242 | 65 |
| clonidine | 6.4 | 6200 | 969 |

The results show that the d-enantiomer is an extremely selective $\alpha_2$-agonist compared to medetomidine and the other reference compounds.

3. SEDATIVE ANALYGESIC EFFECTS

The sedative-analgesic properties of the compounds were studied in the spontaneous motility and writhing-test in the mouse. Spontaneous motility of mice and rats was measured using the Animex-activity meter. The test compounds were administered i.p. 30 minutes before the measuring periods of two minutes. In the writhing test the compounds studied and saline were administered s.c. to rats, and 45 min. later 1 ml of 1% acetic acid was administered i.p. The number of writhes was recorded in the following 25 min. period (Koster et al., Fred. Proc. 18: 412, 1959). Results are shown in Tables 3 and 4.

TABLE 3

| ED$_{50}$ -values of the studied compounds in reducing spontaneous motility in mice | |
| --- | --- |
| Compound | ED$_{50}$ (mg/kg s.c.) |
| d-enantiomer | 0.02 |
| l-enantiomer | >10 |
| medetomidine | 0.05 |
| detomidine | 0.3 |
| clonidine | 0.3 |

TABLE 4

| ED$_{50}$-values of the studied compounds in acetic acid-induced writhing test in mice | |
| --- | --- |
| Compound | ED$_{50}$ (mg/kg s.c.) |
| d-enantiomer | 0.01 |
| l-enantiomer | >10 |
| medetomidine | 0.02 |
| detomidine | 0.02 |
| clonidine | 0.03 |

These results shown that the d-enantiomer has an enhanced sedative/analgesic property compared to the racemic mixture (medetomidine) and other reference compounds. The sedative/analgesic effects of medetomidine are confined to the d-enantiomer.

4. ANXIOLYTIC EFFECTS

The anxiolytic effects of the compounds were studied using a method described by Handley and Mithoni: Naunyn-Schmiedeb, Arch. Pharmacol. 327, 1–5, 1984. In this test the manner of exploration of open and enclosed arms in an elevated t-maze by a rat is examined. It has been shown that anxiolytic drugs increase the relative exploration of open arms. A rat is placed in the center of the t-maze and the number of open and enclosed entries is recorded during 5 minutes. Results obtained are shown in Table 5.

TABLE 5

| Drug/dose, mg/kg | Mean number of entries (n = 6) | | | |
| --- | --- | --- | --- | --- |
| | open | closed | total | open/total |
| NaCl | 3.4 | 8.6 | 12.0 | 0.28 |
| d-enantiomer | | | | |
| 0.0003 | 4.8 | 10.6 | 14.0 | 0.20 |
| 0.001 | 3.2 | 10.6 | 13.8 | 0.23 |
| 0.003 | 4.0 | 9.5 | 13.5 | 0.29 |
| 0.01 | 5.8 | 8.8 | 14.6 | 0.39 |
| 0.03 | 2.5 | 3.0 | 5.5 | 0.45 |
| diazepam | | | | |
| 1 | 5.2 | 10.5 | 15.7 | 0.33 |

The results show that the d-enantiomer has an anxiolytic profile in the elevated t-maze test.

It is well known that anxiety states connected to withdrawal symptoms are due to noradrenergic hyperactivity. Therefore such symptoms can be successfully treated with drugs reducing the level of noradrenaline, e.g. clonidine. Experiments in the rat indicate that the d-enantiomer is able to reduce noradrenaline release and thus sympathetic tone both in the central and peripheral nervous systems. This has clearly been demonstrated by measuring CSF-concentrations of MHPG-SO$_4$ (the principal metabolite of central noradrenaline) in the rat after d-enantiomer administration. The results are shown in Table 6.

TABLE 6

| d-enantiomer dose µg/kg | CSF MHPG-SO$_4$ (% of control) (4 h after d-enantiomer adm.) |
| --- | --- |
| 0 | 100 |
| 3 | −10 |
| 10 | −20 |
| 30 | −30 |
| 100 | −65 |

5. ANTIHYPERTENSIVE EFFECTS

The antihypertensive properties of the compounds of the invention have been studied as follows: Sprague-Dawley rats of normal weight were first anesthetized with urethane. After this, the femoral artery was connected by a polyethylene tube to a blood pressure transducer. The test substance was then injected into the femoral vein and the blood pressure and the pulse frequency were registered with a recorder. Results are shown in Table 7.

TABLE 7

| Antihypertensive effects of the d-enantiomer in anesthetized rats | | |
| --- | --- | --- |
| Dose, mg/kg | Decrease in BP, % | Decrease in heart rate, % |
| 0.001 | −8 | −21 |
| 0.003 | −23 | −40 |
| 0.01 | −43 | −47 |
| 0.03 | −45 | −48 |
| 0.1 | −45 | −50 |

The results show that the d-enantiomer possesses clear anti-hypertensive and bradycardia effects.

The d- and l-enantiomers, and their non-toxic, pharmaceutically acceptable acid addition salts or mixtures thereof may be administered parenterally, intravenously or orally. Typically, an effective amount of the compound is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc. and of course the structure of the derivative.

The pharmaceutical carriers which are typically employed with the compounds of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well known to those skilled in the art of pharmaceutical formulations. The combination of the derivative and the carrier may be fashioned into numerous acceptable forms, such as tablets, capsules, suppositories, solutions, emulsions, and powders.

The following Example illustrates the separation of the new enantiomers.

EXAMPLE 14 g of medetomidine (base) were dissolved in 50 ml of methanol. 10.5 g of (+)-tartaric acid were dissolved in 50 ml of methanol. The solutions were mixed and the solvent was evaporated to a volume of 50 ml. The mixture was put into an ice bath and 9 g of white precipitate was obtained. The precipitate was suspended in 25 ml of ethanol, the mixture was kept in ultrasonic sound for 14 min and filtered. The precipitate was dissolved in a mixture of 20 ml abs. ethanol and 60 ml methanol by heating on a steam bath. After cooling, 5 g of precipitate (degree of rotation +55°) was obtained. After recrystallization from 60 ml of methanol, 4.1 g of product was obtained, degree of rotation +60°. Recrystallization was repeated until the degree of rotation did not increase any longer. The d-enantiomer tartrate was dissolved in water, the solution was made alkaline and the d-enantiomer was dissolved in an organic solvent e.g. dichlormethane or diethyl ether. The degree of rotation of the d-enantiomer base was +75°.

The l-enantiomers may be isolated from the mother liquors.

We claim:

1. The d enantiomer of medetomidine or a non-toxic pharmaceutically acceptable acid addition salt thereof.

2. A pharmaceutical composition suitable for use in a method of sedation/analgesia or treatment of anxiety or hypertension comprising the d-enantiomer of medetomidine or a non-toxic pharmaceutically acceptable acid addition salt thereof in an amount sufficient to produce the desired effect in association with a pharmaceutical carrier.

3. A method of sedation/analgesia or treatment of anxiety or hypertension by administration to a subject of an effective amount of an enantiomer according to claim 1.

4. A method of sedation/analgesia or treatment of anxiety or hypertension by administration to a subject of an effective amount of a composition according to claim 2.

* * * * *